United States Patent [19]

Miyatake et al.

[11] Patent Number: 4,794,255
[45] Date of Patent: Dec. 27, 1988

[54] ABSORPTION ANALYZER

[75] Inventors: Kimio Miyatake; Takao Imaki; Kenji Takeda, all of Kyoto, Japan

[73] Assignee: Horiba, Ltd., Kyoto, Japan

[21] Appl. No.: 935,301

[22] Filed: Nov. 26, 1986

[30] Foreign Application Priority Data

Nov. 27, 1985 [JP] Japan .................. 60-267640

[51] Int. Cl.⁴ ............................................. G01J 3/00
[52] U.S. Cl. ...................................... 250/343; 250/345
[58] Field of Search ...................... 250/343, 344, 345; 356/437, 439

[56] References Cited

U.S. PATENT DOCUMENTS 4,271,124 6/1981 Specter ............................ 250/343
4,297,577 10/1981 Coe et al. ........................ 250/343
4,514,635 4/1985 Ishida et al. ..................... 250/343

FOREIGN PATENT DOCUMENTS 49-25349 7/1974 Japan.
59-23380 6/1984 Japan.

Primary Examiner—Janice A. Howell
Attorney, Agent, or Firm—Wenderoth, Lind & Ponack

[57] ABSTRACT

The absorption analyzer of the type provided with light sources (3a, 3b), cells (1, 2) containing a reference gas and an ingredient gas to be measured, respectively and a detector (5) for determining the absorption of the light emanating from the light sources and passing through the cells, is additonally equipped with a gas filter (8) arranged in the optical path between said light sources and the detector and contains an ingredient gas with an absorption spectrum band that nearly corresponds to that of an ingredient gas to be measured or an ingredient to be measured. The advantage of the invention is that a relatively large range of concentrations of gas ingredients can be measured with the same type of cells having the same cell length.

7 Claims, 1 Drawing Sheet

ABSORPTION ANALYZER

BACKGROUND OF THE INVENTION

1. Field of the Invention

The present invention relates to an absorption type gas analyzer using infrared rays, ultraviolet rays and the like.

2. Description of the Prior Art

In an absorption type gas analyzer, for example an infrared gas analyzer, the absorption of infrared rays incident upon the inside of a cell from a light source by a sample gas contained in the cell is measured to determine the concentration of an ingredient gas contained in the sample gas. This absorption type gas analyzer is fundamentally based on Lambert-Beer's law. That is to say, provided that an intensity of the incident ray is $I_o$, in a cell having a length l, an absorptivity constant K (the constant determined by a measuring-wave length and an object to be measured), and a gas-concentration being C, the intensity of the transmitted ray I is expressed by the following equation:

$$I = I_o e^{-KCl}$$

Accordingly, in an absorption gas type analyzer, the relation between the concentration of an ingredient gas to be measured and the output of the transmitted light has a larger curvature with an increase of the concentration of an ingredient gas to be measured, as shown in FIG. 2. In order to improve the accuracy of measurement by using an almost linear portion of the curve shown in FIG. 2, the cell length is reduced when the concentration of an ingredient gas to be measured is high while the cell length is increased when the concentration of an ingredient gas to be measured is low.

A prior art absorption analyzer, in which the cell length is changed in correspondence with the concentration of an ingredient gas to be measured in a sample gas, is disclosed in for example Japanese Utility Model Publication No. 49-25349. In such a prior art device a plurality of cells are arranged in series between a light source and a detector and the cells to be used are changed in correspondence to the cocentration of the ingredient gas to be measured in a sample gas.

However, this prior art device has exhibited disadvantages in that since the cells are arranged in series, the analyzer must be large-sized and overly long as a whole, and a troublesome operation is required in order to change the cell-length in correspondence to the concentration of the ingredient gas to be measured. In addition, although the provision of an interference filter sideways a light source is disclosed in the above-described Japanese Patent Publication, merely an influence of an interference spectrum upon the measurement is eliminated by previously removing an interference spectrum band overlapping on an absorption spectrum band of an ingredient gas to be measured, but other effects are not achieved.

SUMMARY OF THE INVENTION

It is an object of the present invention to provide an absorption type gas analyzer capable of measuring the concentration of an ingredient gas over a wide range of concentrations from a lower concentration to a higher concentration, by means of a single cell without changing a cell length.

An absorption analyzer according to the present invention comprises at least one light source, at least one gas cell and a detector for determining the absorption of the light emanating from said light source and passing through said gas cell and is characterized in that a gas filter is provided in the optical path between said light source and said detector, said gas filter comprising a housing and containing an ingredient gas having an absorption spectrum band that nearly corresponds to that of an ingredient gas to be measured or an ingredient to be measured.

According to the present invention, as described above, in an absorption type gas analyzer provided with a light source, a cell and a detector, a beam of light from the light source is passed through the gas filter filled with a gas having an absorption spectrum band nearly equivalent to an absorption spectrum band of the ingredient gas to be measured or the ingredient in the sample gas, the concentration of which is to be measured. For reasons discussed below, an ingredient gas having higher concentrations in the sample gas can be measured with high accuracy by means of an absorption type gas analyzer having a cell length suitable for measuring the concentration of the ingredient gas when having lower concentrations without changing the cell length. With this the invention, the problem of changing the cell-length in correspondence to the concentration of the ingredient gas in the sample gas is overcome. That is to say, a wide range of concentrations to be measured from lower concentrations to higher concentrations, of the ingredient gas can be measured with high accuracy by means of cells having the same length by merely changing the concentration of the gas enclosed in the gas filter.

DESCRIPTION OF THE PREFERRED EMBODIMENT

Figure 1:
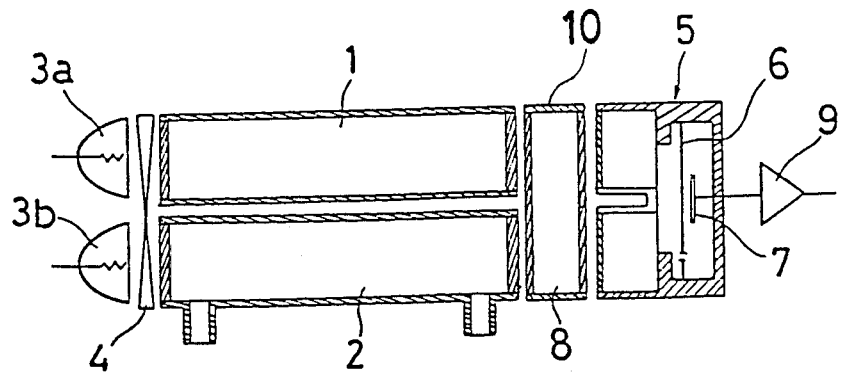
FIG. 1 is a diagrammatic sectional view showing a preferred embodiment of the present invention.

The presently preferred embodiment of an absorption analyzer according to the invention is described with reference to an infrared gas analyzer as shown in FIG. 1.

Referring to FIG. 1, reference numeral 1 designates a reference cell filled with a gas, such as $N_2$, which does not absorb infrared rays. A sample cell 2 is supplied with a sample gas. Light sources 3a, 3b are arranged on one side of the reference cell 1 and the sample cell 2, respectively. Beams of light radiating from these light sources 3a, 3b are transmitted as to intermittent beams after passing through a rotating sector 4, the intermittent beams in turn passing through the reference cell 1 and the sample cell 2, respectively, to alternately enter a condenser microphone 5 arranged on the other side of the reference cell 1 and the sample cell 2 as a detector.

Reference numeral 6 designates a condenser film and reference numeral 7 designates a fixed pole.

A gas filter 8 is arranged between the reference cell 1 and the sample cell 2 and the condenser microphone 5. A gas having an absorption spectrum band nearly equivalent to that of an ingredient gas, the concentration of which is to be measured, or an ingredient, the concentration of which is to be measured, is enclosed in the gas filter 8. When the ingredient, the concentration of which is to be measured, is a stable gas such as CO or $CO_2$, the gas filter 8 enclosed the ingredient gas. On the other hand in the case where the ingredient, the concentration of which is to be measured, is unstable, e.g. cyan gas, the gas filter 8 can be used with an acetylene gas loading having an absorption spectrum band nearly equivalent to that of the ingredient gas. Reference numeral 9 designates an amplifier.

With the above-described construction, when the sample cell 2 is supplied with the sample gas, infrared rays emitted from the light source 3a are not absorbed in the reference cell 1 but pass through the gas filter 8 to be absorbed in amounts corresponding to the concentration of the gas in the gas filter 8, whereby the condenser film 6 is dislocated. On the other hand, infrared rays emanating from the light source 3b are absorbed in the sample cell 2 in amounts corresponding to the concentration of the ingredient gas contained in the sample gas which is to be measured and pass through the gas filter 8 to be absorbed again, and then the infrared rays enter the condenser microphone 5 to dislocate the condenser film 6. The concentration of the ingredient gas contained in the sample gas is measured from a difference in the dislocation of the condenser film 6.

A gas of higher concentration of gas is enclosed in said gas filter 8 when the concentration of the ingredient gas in the sample gas, which is to be measured, is higher while a lower concentration of gas is enclosed in the gas filter 8 when the concentration of the ingredient gas in the sample gas is lower.

For example, when the cell-length is 10 mm and the ingredient gas, the concentration of which is to be measured, is $CO_2$, $CO_2$ gas having a concentration of 5% by volume is enclosed in the gas filter 8 in a case of a full scale of 20% by volume (for use in a higher-concentration measurement), $CO_2$ gas having a concentration of 3% by volume in a case of a full scale of 15% by volume (for use in a middle-concentration measurement), and $CO_2$ gas is not enclosed in the gas filter 8 in a case of a full scale smaller than several % by volume (for use in a superlower-concentration measurement).

In addition, although the concentration of the ingredient gas to be measured in a sample gas is unknown, it can be initially roughly estimated depending upon the type of sample gas, such as air, smoke from a plant or exhaust gas from a motorcar, so that the concentration of the gas to be enclosed in the gas filter may be selected in correspondence to the estimated concentration.

Figures 2, 3:
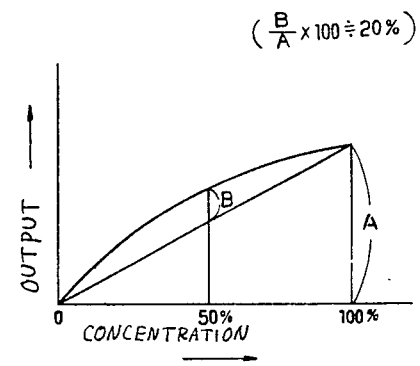
FIG. 2 is a graph showing the relation between the output of a conventional absorption type gas analyzer and the concentration of an ingredient gas to be measured in the sample gas.
FIG. 3 is a graph showing the relation between the output of an absorption type gas analyzer according to the present invention and the concentration of an ingredient gas to be measured in the sample gas.
Figure 4:
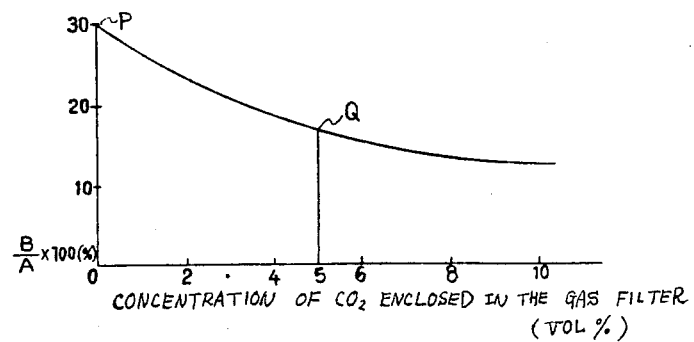
FIG. 4 is a graph showing the relation between the concentration of $CO_2$ enclosed in a gas filter and a calibration curve.

FIG. 4 is a graph showing a relation between a concentration of $CO_2$ (one example of an ingredient gas to be measured) enclosed in a gas filter 8 and calibration curves as shown in FIGS. 2, 3. More specifically, a ratio of B to A, that is to say $B/A \times 100$ (%), as shown in FIGS. 2, 3 is plotted along the ordinate while the concentration (Vol %) of $CO_2$ enclosed in the gas filter 8 is plotted along the abscissa. And, referring to FIG. 4, a point P shows a bending extent of the calibration curve at a 50%-full scale point in FIG. 2 ($B/A \times 100 \approx 30\%$) while a point Q shows a bending extent of the calibration curve at a 50%-full scale point in FIG. 3 ($B/A \times 100 \approx 20\%$).

As seen from FIGS. 2, 3, the bending extent of the calibration curve increases (the linearity is lowered) with an increase in the concentration of the ingredient gas in the sample gas. On the other hand, as seen from FIG. 4, the bending extent of the calibration curve is reduced with an increase in the concentration of the gas enclosed in the gas filter 8 (but an output is reduced). Accordingly, as described above, when the concentration of the ingredient gas in the sample gas is higher, a gas also having a higher concentration is enclosed in the gas filter 8 while when the concentration of the ingredient gas to be measured in the sample gas is lower, the same gas but having a lower concentration is enclosed in the gas filter. In fact, it is desirable that said concentration of the gas to be enclosed in the gas filter 8 be set so that the bending extent ($B/A \times 100$) of the calibration curve is 20% or less and the reduction of the output is not increased.

In this way, the accuracy of measurement is improved by setting the concentration of the gas enclosed in the gas filter 8 at an amount corresponding to the concentration of the ingredient gas contained in the sample gas.

Accordingly, also $CO_2$, of which the concentration in a sample gas can be comparatively large, which up until now had to be measured with a short cell, can now be measured with high accuracy without changing the cell length by using an infrared ray analyzer for use in the determination of CO having lower concentrations, in which a cell is formed having a comparatively large length, and providing a gas filter in the optical path of the infrared ray analyzer.

Although a condenser microphone is used as a detector in the above-described preferred embodiment, optional detectors, such as a solid state detector using a pyroelectric detector, a semiconductor detector, a thermopile and the like may be used. Also, the present invention may be applied to a "fluid-modulation type analyzer" in which a pair of cells are alternately supplied with a reference gas and a sample gas or a single cell is alternately supplied with a reference gas and a sample gas. In addition, the gas filter 8 can be constructed as an integrated unit with the detector 5. Besides, the gas filter 8 may be arranged between the rotating sector 4 and the reference cell 1 and the sample cell 2. Furthermore, ingredient gas, and the like may be enclosed in a housing surrounding the light source to form the gas filter.

What is claimed is:

1. An absorption type gas analyzer for measuring the concentration of a component in a sample gas, said analyzer comprising:
   at least one gas cell comprising a sample gas cell for containing the sample gas having the component;
   at least one light source comprising a light source for radiating light along an optical path that passes through said sample gas cell, a portion of the light being absorbed in said sample gas cell in an amount corresponding to the concentration of the component in the sample gas and a remaining portion of the light passing from said sample gas cell;
   a gas filter disposed in said optical path, said gas filter comprising a housing containing an ingredient gas having an absorption spectrum band an absorption spectrum band corresponds substantially to that of the component; and a detector disposed in said optical path for receiving the light after passing through said sample gas cell and said gas filter, and for detecting the amount of the light that has been absorbed.

2. An absorption type gas analyzer as claimed in claim 1,
wherein said at least one gas cell also comprises a reference gas cell for containing a reference gas, said at least one light source also comprises a light source for radiating light along an optical path that passes through said reference gas cell and to said detector, and said gas filter is disposed in said optical paths between said gas cells and said detector.

3. An absorption type gas analyzer as claimed in claim 1,
wherein said at least one gas cell also comprises a reference gas cell for containing a reference gas, said at least one light source also comprises a light source for radiating light along an optical path that passes through said reference gas cell and to said detector, and said gas filter is disposed in said optical paths between said light sources and said gas cells.

4. An absorption type gas analyzer as claimed in claim 1,
wherein said detector is a condenser microphone.

5. An absorption type gas analyzer as claimed in claim 2,
wherein said detector is a condenser microphone.

6. An absorption type gas analyzer as claimed in claim 3,
wherein said detector is a condenser microphone.

7. An absorption type gas analyzer as claimed in claim 1,
wherein said detector is a solid state detector.

* * * * *